United States Patent [19]

Danziger

[11] Patent Number: 5,344,534

[45] Date of Patent: Sep. 6, 1994

[54] GEL ELECTROPHORESIS MEASUREMENT OF DYNAMIC REACTION PRODUCT BY CONTINUOUS SAMPLING

[76] Inventor: Robert S. Danziger, 20 W. 64th St., Apt. 15K, New York, N.Y. 10023

[21] Appl. No.: 27,284

[22] Filed: Mar. 5, 1993

[51] Int. Cl.⁵ ............................................. C25B 7/00
[52] U.S. Cl. ............................ 204/182.8; 204/299 R; 436/52; 436/161; 436/517
[58] Field of Search ..................... 204/299 R, 182.8; 436/52, 161, 517

[56] References Cited

U.S. PATENT DOCUMENTS

| | | | |
|---|---|---|---|
| 3,432,414 | 3/1969 | Rand | 204/299 |
| 4,061,561 | 12/1977 | Fletcher et al. | 204/299 |
| 4,124,470 | 11/1978 | Dahms | 204/180 R |
| 4,199,428 | 4/1980 | Hayashi et al. | 204/299 R |
| 4,631,120 | 12/1986 | Pohl | 204/182.8 |
| 4,735,697 | 4/1988 | Burton | 204/182.8 |
| 4,824,547 | 4/1989 | Zhang et al. | 204/299 R |
| 4,867,855 | 9/1989 | Burton | 204/182.8 |
| 4,883,577 | 11/1989 | Sugimoto et al. | 204/299 R |
| 4,911,807 | 3/1990 | Burd | 204/180.1 |
| 4,938,080 | 7/1990 | Sarrine et al. | 73/864.2 |

*Primary Examiner*—John Niebling
*Assistant Examiner*—C. Delacroix-Muirheid
*Attorney, Agent, or Firm*—Dennis T. Griggs

[57] ABSTRACT

A kinetic reaction mixture is sampled continuously for determining the effect of a specific agent on the population density of a bio-organic molecule of interest as a function of time. A reaction sample containing the molecule of interest is processed through a high performance liquid chromatography column which produces longitudinal separation of a specific bio-organic molecule of interest. A continuous stream of longitudinally separated bio-organic molecules having a specific property of interest is delivered as a flowing stream into longitudinally separated sample receiving apertures formed in the face of a gel slab. Movement of the delivery nozzle and separation of the sample receiving apertures cause sample batches of reaction products to be deposited within separate channels, with the number of receiving channels corresponding generally with the number of discrete sample time intervals. The bio-organic molecules are clustered in discrete bands along the length of each receiver channel, with the vertical thickness of each band corresponding generally to the population density of the subject molecule during a specific time interval of the kinetic reaction.

6 Claims, 2 Drawing Sheets

GEL ELECTROPHORESIS MEASUREMENT OF DYNAMIC REACTION PRODUCT BY CONTINUOUS SAMPLING

FIELD OF THE INVENTION

This invention relates generally to gel electrophoresis, and in particular to gel electrophoresis method and apparatus for measuring dynamic changes in high molecular weight components during a kinetic reaction.

BACKGROUND OF THE INVENTION

Electrophoresis procedures are known for separating and analyzing proteins, nucleic acids and their reaction products based on differences in net surface charge, known as isoelectric focusing, and also based on differences in molecular size. Electrophoresis is a commonly used technique to separate proteins and other macromolecules (e.g. DNA and PAPA) based on the phenomenon that a molecule with a net charge will move in an electric field. The velocity v of migration of a protein (or any molecule) through a gel medium in the presence of an electric field is determined by the net charge z on the molecule, electric field strength E and frictional coefficient f. The general relationship may be stated as follows:

$$V = Ez/f$$

That is, the charged molecule will be propelled toward the oppositely charged field electrode by the electric field force (Ez). Its movement is opposed by viscous drag (fv) arising from friction between the moving molecule and the medium. The frictional coefficient depends on the viscosity of the medium and both the shape and mass of the molecule.

Isoelectric focusing relies on the property of certain bio-organic molecules, such as proteins and peptides, which have a three-dimensional structure on which ionizable surface groups (e.g., carboxyl, amino, imidazole, guanidinium) are clustered. These ionizable groups are amphoteric in nature and carry a net electrical charge, either positive or negative. At a unique gel pH value, called the isoelectric point, the net charge of surface groups is neutralized.

The isoelectric separation process is carried out by migration of the bio-organic molecules through a buffered gel substrate. A commonly used substrate is polyacrylamide gel. This gel consists of a mixture of acrylamide monomer and an appropriate cross-linking agent. The gel may be enclosed within a capillary tube or between parallel glass plates. The polyacrylamide gel is buffered with an ampholyte agent. Ampholyte consists of a mixture of low molecular weight amphoteric compounds having isoelectric points distributed over a predetermined range of pH values. The application of a constant-voltage, DC electric field across an ampholyte-buffered gel causes the ampholytes to shift and locate according to their specific leoelectric points, thereby establishing a pH gradient with sufficient buffering capacity and conductance for focusing the bio-organic molecules at their respective isoelectric points.

Isoelectric focusing has the effect of separating the bio-organic molecules with different electric charges into discrete bands along the length of the gel, with each band containing molecules having the same isoelectric point.

The bio-organic molecules may also be separated according to their different molecular weights by migration of the proteins through a gel slab which acts as a sieve. During migration through the gel, the different bio-organic molecules having different molecular weights produce separate clusters along the gel slab. Each cluster contains purified proteins having substantially the same molecular weight.

Electrophoretic separations are usually performed in gels since they function as molecular sieves that enhance separation. Molecules that are small compared to the pores in the gal move readily through the gel, while molecules larger than the pores are virtually immobile. The net result is that small proteins migrate further than large ones. Pore sizes of the gel can be controlled during gel production.

The gel slabs are usually made from polyacrylamide since it is chemically inert and readily formed by polymerization of acrylamide. Pore sizes are controlled by the concentration of acrylamide and methylenebisacrylamide (a cross-linking reagent) during polymerization. The gel slab is supported vertically and samples are placed on the exposed face of the gel slab. Current is applied such that the bottom of the gel slab is the anode; the negatively charged molecules migrate toward the bottom of the gel slab.

Protein bands are visualized by staining with silver or a dye such as Coomassie blue. Nucleic acid bands may be visualized with ultraviolet light and edthenium bromide staining. In addition, protein bands may be labeled with a radioactive tag for autoradiography or antibodies (Western blot), and nucleic acid bands may be labelled with antisense oligonucleotides (Northern and Southern blots).

Another separation technique which is useful for separating bio-organic molecules is known as high performance liquid chromatography. According to this technique, a mobile phase eluate, into which a bio-organic sample to be analyzed has been injected, is forced through a bed of micro-particulate chromatographic packing material at a predetermined linear velocity. The separation of components according to this technique depends on the eluate chemistry and the properties of the packing material utilized. Proteins and other bio-organic molecules may be separated by this procedure on the basis of molecular size, ionic properties, absorptive characteristics and hydrophobicity.

DESCRIPTION OF THE PRIOR ART

A parameter of interest in certain kinetic reactions is the time variation of the population of selected bio-organic molecules, for example, proteins and peptides. For example, it may be desirable to determine the kinetic response of a bio-organic mixture, when exposed to a specific agent, for example, norepinephrine. That is, it is desirable to determine the time varying population of bio-organic molecules which are formed or depleted as a consequence of the reaction of the sample mixture with an active agent over a specific reaction time interval.

The rate of formation of product or depletion/degradation of a substrate is used to characterize dynamic biological/chemical reactions. The rate at which a given protein (e.g. troponin I) is phosphorylated in a suspension of cells (e.g. muscle cells) or the rate at which a compound is degraded by a given enzyme in a reaction are typical examples.

If the substrate and product in a reaction display different electrophoretic mobilities, electrophoresis may be used to measure the quantity of the substrate and reaction products. According to conventional techniques, to measure reaction kinetics with electrophoresis, the reaction mixture is sampled for electrophoresis at discrete time points and the time course between the sample times interpolated. This procedure is limited by the number of discrete time points that can be sampled in order to characterize the time course of the reaction.

According to conventional techniques, it has been possible to obtain a "snapshot" of a specific bio-organic molecule population at a specific point in time during a kinetic reaction by manually drawing a sample of the mixture and separating the various molecules according to size by conventional gel electrophoresis. One limitation of that procedure is the lack of specific component resolution inasmuch as multiple bio-organic molecules of substantially the same size may be present, but only one of which may be of interest. That is, the population of a specific bio-organic molecule may be masked or obscured by the presence of other kinds of bio-organic molecules, thus making identification and comparison more difficult. Another limitation is that the kinetic reaction may undergo rapid changes between manual samples. That is, the specific populations of interest may change substantially during the time interval between manually executed samples, and significant information may be lost. Moreover, if only a few manual samples are taken, the data collected may not be representative of the true population range.

OBJECTS OF THE INVENTION

The principal object of the present invention is to provide a method and apparatus for continuous sampling of a reaction product for the determination of reaction kinetics by gel electrophoresis.

A related object of the present invention is to provide a method and apparatus for determining the population variation as a function of time of a specific bio-organic molecule in a mixture which is undergoing a kinetic reaction.

Another object of the present invention is to improve the sample resolution of a specific bio-organic molecule of interest taken from a reaction mixture containing a variety of bio-organic molecules.

SUMMARY OF THE INVENTION

The foregoing objects are achieved according to one aspect of the present invention by continuous uninterrupted measurement of the electrophoretic properties (e.g. electrophoretic mobility of proteins/molecules) of a reaction mixture. A continuous and uninterrupted sampling of a reaction mixture is accomplished by the continuous withdrawal of a sample product stream from a reaction mixture and delivery of the sample product stream from a moving carrier onto a gel slab. Both the rate of carrier travel across the gel slab and rate of withdrawal of sample product from the reaction mixture are carefully controlled so that the reaction mixture is sampled continuously during a predetermined time interval which corresponds with the reaction kinetics. That is, a continuous sample of the reaction solution is delivered by the moving carrier to an initial slab location at the onset of the reaction and the sample stream is terminated when the last slab receiving location has been loaded upon termination of the reaction.

According to another aspect of the invention, a reaction mixture containing a bio-organic molecule of interest is sampled continuously during the course of a kinetic reaction for determining the effect of a specific agent on the population of the bio-organic molecule of interest as a function of time. A sample stream is pumped or otherwise drawn from a reservoir in which the kinetic reaction occurs, and is delivered as a flowing stream to the input of a high performance liquid chromatography column for producing longitudinal separation of the specific bio-organic molecule of interest. Depending on the type of chromatography packing materials used, the molecules of interest are separated on the basis of a specific physical parameter, for example molecular size, ionic properties, absorptive characteristics and hydrophobicity.

A continuous stream of longitudinally separated bio-organic molecules having a specific property or parameter of interest is delivered by a moving carrier and loaded onto the sample capture medium of an electrophoresis gel slab. The surface of the gel slab is modified with a comb to produce discrete sample receiving apertures. The flow rate of the longitudinally separated sample eluate and the rate of travel of the moving delivery carrier relative to the receiving surface of the gel slab are carefully controlled so that the sample reaction product is delivered continuously over a predetermined time interval which corresponds with a predetermined kinetic reaction time interval. That is, a continuous sample of the reaction product taken at the onset of the kinetic reaction is delivered by the moving carrier to the initial receiving aperture and subsequently to intermediate apertures. The sample stream is terminated when the last receiving aperture has been filled with reaction product taken upon termination of the kinetic reaction.

The continuous stream of reaction eluate is processed through the high performance liquid chromatography column, whereby the molecular reaction products of interest are separated in longitudinally spaced batches and are loaded continuously into the receiving apertures of the electrophoresis gel. The delivery flow rate and rate of travel of the moving carrier relative to the electrophoresis gel are carefully controlled so that the batches of sample reaction product stream are delivered continuously over a predetermined reaction time interval, with all of the receiving apertures being filled substantially uniformly during the course of the kinetic reaction.

Although the delivery of the reaction product stream is continuous, the movement of the carrier and separation of the sample receiving apertures causes reaction products containing batches of bio-organic molecules of interest to be deposited within separate channels. The number of receiving channels corresponds generally with a predetermined number of discrete sample time intervals, and a number (population) of bio-organic molecules of interest are contained within each sample batch. After the last sample receiving aperture has been filled, the gel slab is then subjected to an electric field. Gel electrophoresis of the time variant samples then proceeds according to conventional practice. The protein molecules are clustered in discrete bands along the length of each receiver channel, with the vertical thickness of each band corresponding generally to the population density of the target molecule in the reaction mixture during a specific time interval of the kinetic reaction. Thus, the population variation of a specific bio-organic molecule of interest from onset to termination of a specific kinetic reaction may be determined.

DETAILED DESCRIPTION OF THE PREFERRED EMBODIMENTS

Figure 1:
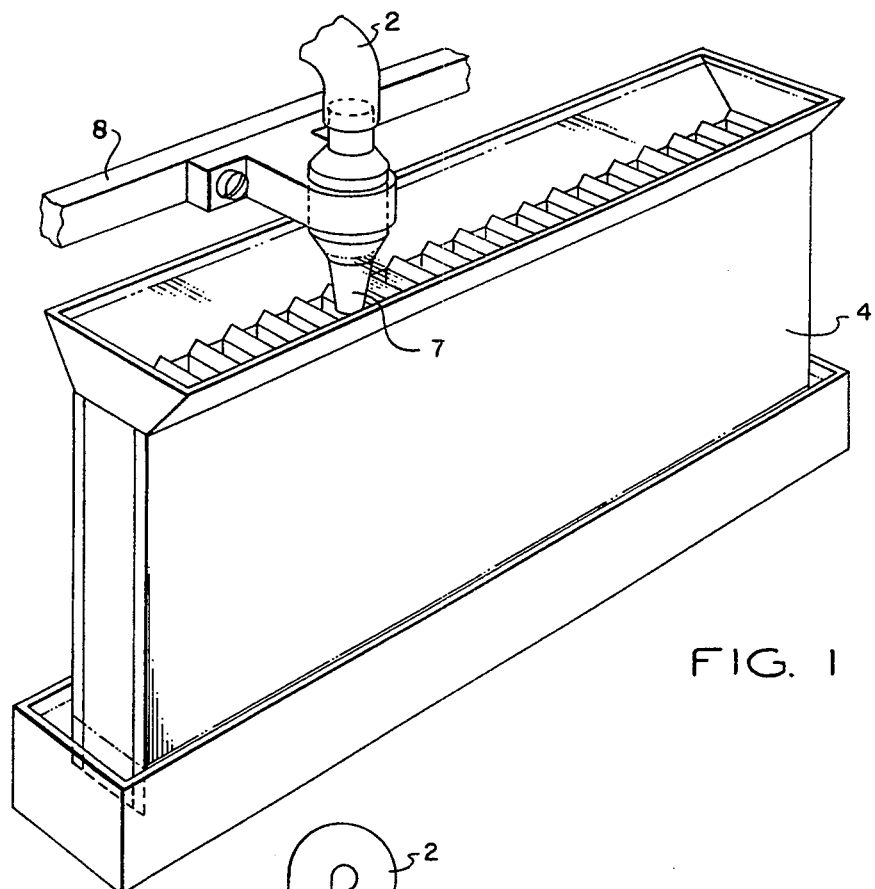
FIG. 1 is a perspective view illustrating the delivery of a continuous sample stream of reaction product onto the inlet face of a gel electrophoresis slab.
Figure 2:
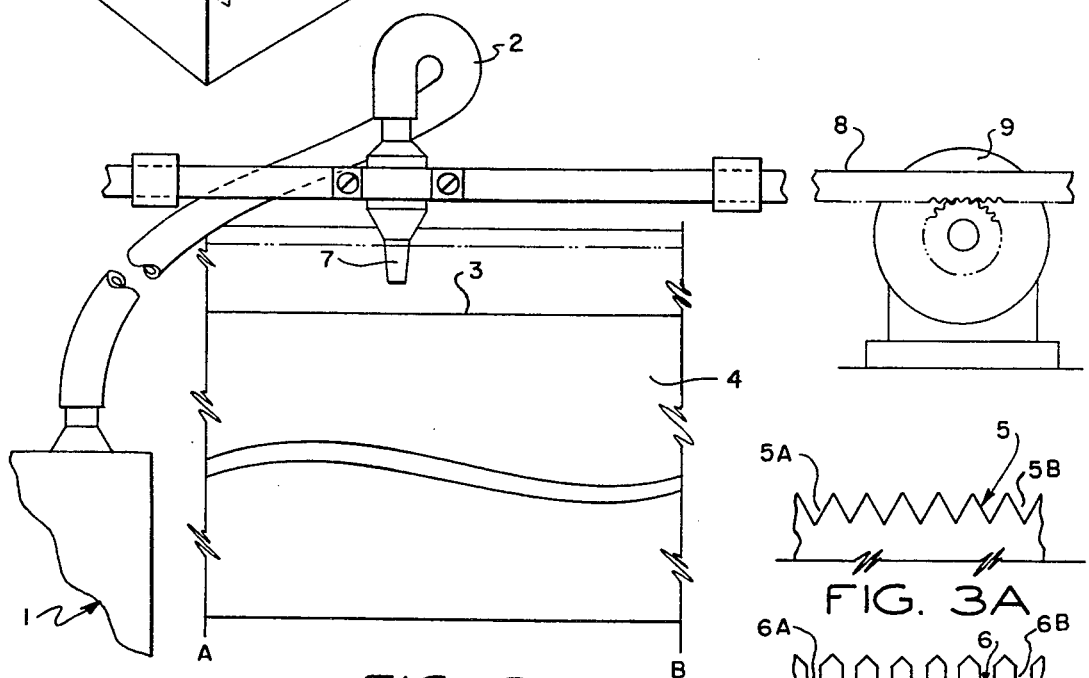
FIG. 2 is a front elevational view thereof, partially broken away.

Referring now to FIG. 1 and FIG. 2, a reaction mixture containing proteins or nucleic acids is undergoing a reaction (e.g. a suspension of cell fragments to which norepinephrine has been added to cause time dependent, phosphorylations of myofilament proteins) within a reservoir 1. A flowing sample stream from the reaction mixture is pumped from the reservoir through a flexible flow line 2 (i.e. plastic tubing) at a predetermined flow rate. A heating element may be coupled to the plastic tubing or to the reservoir to heat and denature the sample (i.e. for protein electrophoresis). A separate chamber may also be added for addition of a denaturing solution.

Figure 3A:
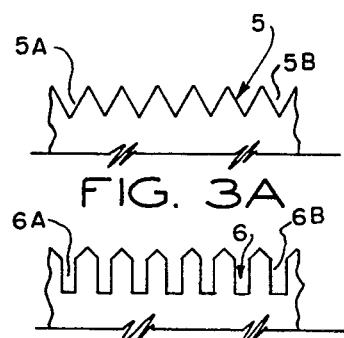
FIG. 3A is an elevational view of a gel electrophoresis slab having a modified inlet receiving face.
Figure 3B:
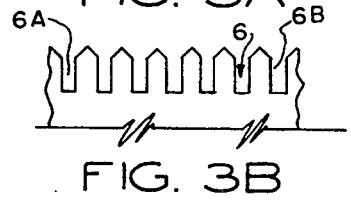
FIG. 3B is a view similar to FIG. 3A of an alternative inlet face arrangement; and, FIG. 4 is a simplified schematic diagram of one embodiment of the present invention.

The sample stream is deposited on the inlet face 3 of a gel (i.e. SDS or acrylamide) slab 4, which is modified by receiving apertures as shown in FIGS. 3A, 3B created by the use of a comb at the time of gel formation. According to this arrangement, discrete but contiguous receiving apertures 5 and 6 are formed. As the sample stream is pumped from a delivery nozzle 7 onto the inlet face of the gel slab 4, the delivery nozzle travels from station A to station B, and the sample is deposited into successive apertures 5 or 6 in a continuous manner (i.e. such that sample deposited in an aperture 5A at station A occurs at the onset of the reaction (i.e. when the norepinephrine is added) and in an aperture 5B at station B at the completion of the reaction. The rate at which sample is pumped and travel rate of the nozzle 7 are coordinated so that the apertures are filled during the travel time of the carrier assembly 8 and attached nozzle 7 across the inlet face 3 of the gel slab 4 and that the travel time corresponds to the reaction time. The carrier assembly S is driven by an electric motor 9.

Figure 4:
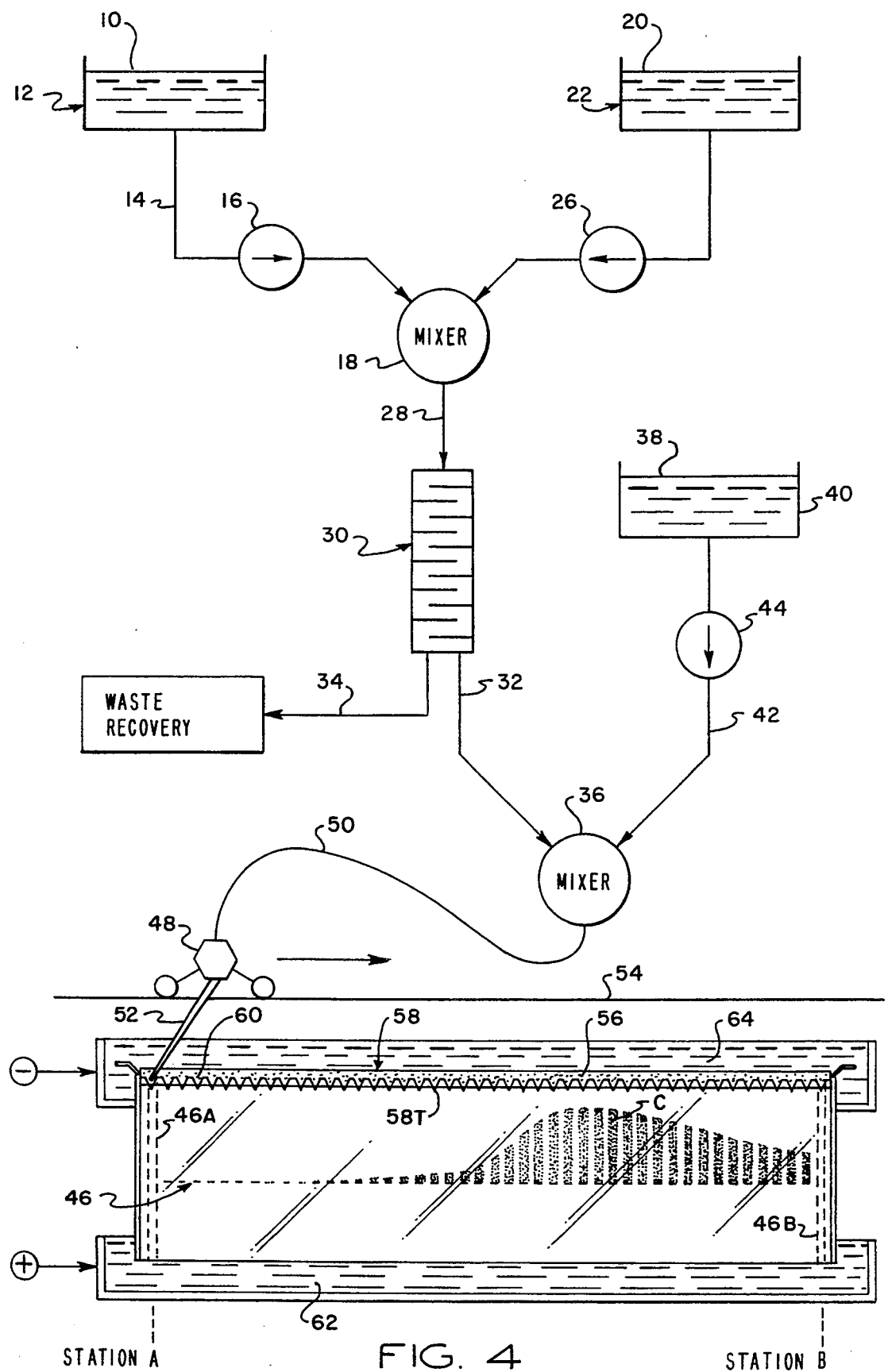

Referring now to FIG. 4, a reaction mixture 10 containing bio-organic molecules, particularly including proteins and nucleic acids which have been mixed with an active agent such as norepinephrine, is undergoing a kinetic reaction within a reservoir 12. A flowing stream of reaction product 10 is pumped from the reservoir 12 through a flow line 14 by a high pressure, low impulse constant flow pump 16. The sample flow stream containing a protein of interest, for example, cAMP, which is to be separated is injected into a mixing chamber 18, with the sample stream being mixed with an eluant 20 taken from a reservoir 22. The eluant 20 is pumped from the reservoir 22 through a delivery conduit 24 by a high pressure, low impulse constant flow pump 26. The eluant 20 is a liquid solvent used for extraction of the protein of interest from others. After the reaction sample is mixed with the eluant, the eluate is delivered by a conduit 28 to a high performance liquid chromatography column 30.

The mobile phase eluate 28 in which the protein sample of interest is carried is forced through a bed of micro-particulate chromatographic packing material at a predetermined velocity, for example, 0.1–0.5 millimeters per second. The type of packing material used and the nature of the eluate determines the basis for separation. Proteins and other bio-organic molecules may be separated in the column 30 on the basis of molecular size (gas permeation chromatography), ionic properties (ion-exchange), absorptive characteristics (absorption chromatography) and hydrophobicity (reverse phase chromatography). A specific chromatographic adsorbent agent is packed within the column 30 for separating the specific protein molecule of interest on the basis of a common physical characteristic or combination of specific characteristics identified above.

As the eluate stream is discharged from the mixer 18, different components in the originally injected reaction product 10 move through the column bed at different velocities as a consequence of their different properties, which causes them to separate. The target molecules are separated and are discharged through an outlet conduit 32 for further processing. The nonselected eluate stream is discharged through a waste recovery conduit 34. The selected fluid sample containing the longitudinally separated components is recovered as a continuously flowing stream and is input to a mixer 36 through the outlet conduit 32.

Before undergoing further processing, the longitudinally separated components output from the column 30 are treated as necessary to provide a substantially uniform net surface charge density. This is particularly important for proteins, which contain relatively large bio-organic molecules having large numbers of amino acid residues. Such proteins have complex formations, and generally do not exhibit a uniform surface charge density in an aqueous medium. A uniform surface charge density is imposed on the longitudinally separated components by mixing with a denaturing solution 38, such as detergent sodium dodecyl sulfate, which is drawn from a reservoir 40. The denaturing solution 38 is pumped through a delivery conduit 42 by a high pressure, low impulse constant flow pump 44. The denaturing solution stream 38 is blended with the longitudinally separated component stream in the mixer 36, and the detergent component of the denaturing solution applies a coating having a uniform charge per unit mass. It may be necessary to heat the blended eluate in a heat exchanger to activate the detergent in the denaturing solution.

The sample product stream containing the denatured, longitudinally separated components is then delivered to a gel slab 46 to undergo accumulation by isoelectric electrophoresis where accumulation in the gel is produced on the basis of net electrical charge. The buffered, denatured reaction product stream is delivered to the gel slab 46 through a movable carriage assembly 48 which is coupled in flow communication to the mixer 36 through a flexible delivery conduit 50. The buffered, denatured reaction sample is then discharged onto the face of the slab 46 through a nozzle 52 as the carriage assembly 48 is moved along a guide track 54 from a first delivery station A to a final delivery station B.

The inlet face of the gel slab 46 is covered by a capture layer 56 of a stacking gel material. The capture layer 56 has a different gel chemistry (pore structure and electrolyte buffer composition) to maximize the rate that the charged components of the treated fluid sample are driven into the gel slab 46. Suitable gel electrolyte materials are presently available and are used in connection with conventional multiphase zone electrophoresis systems.

The inlet face of the gel slab 46 is further modified by a sawtooth comb 58 having multiple teeth 58T which penetrate into the body of the gel. According to this arrangement, discrete triangular sample receiving apertures 60 are formed in the face of the gel slab 46. The body of the slab which lies directly beneath each triangular sample receiving aperture 60 constitutes a discrete channel through which the separated components migrate. Multiple migration channels are defined, with an initial migration channel 46A being aligned with carriage delivery station A, and a terminal migration channel 46B being aligned with the final carriage delivery station B, and with multiple intermediate migration channels being defined therebetween, corresponding with the number of teeth in the comb 58.

The slab assembly consists of the gel slab 46 and the gel capture layer 56. The gel slab 46 may be constructed of any conventional gel material, for example, polyacrylamide. The upper face of the gel slab 46 and the capture medium 56, as well as the lower face of the gel slab 46 are in contact with electrically conductive buffer solutions 62, 64. The continuously flowing stream of buffered, denatured sample reaction product, which is discharged from the nozzle 52, preferably has a density equal to or greater than the density of the upper buffer solution 64. The delivery port of the nozzle 52 is closely spaced to the upper face of the gel slab 46 and is submerged in the gel capture medium 46 so that the reaction sample product is delivered directly into the receiving aperture 60 as it traverses the length of the slab.

After the delivery of the reaction product stream into the receiving apertures has been completed from one end of the slab to the other, an electric field is impressed across the slab by applying positive and negative voltages to separate electrodes which are immersed in the conductive buffer solution 62, 64, respectively. By this arrangement, an electrical field is impressed across the gel slab 46, which causes negatively charged protein molecules to migrate through the gel along the receiving channels. For example, electrophoretic migration of protein molecules may be accomplished by applying approximately 200 volts DC to the conductive buffer solutions 62, 64 for about two hours. The proteins in each receiving channel are clustered about a discrete gel spot within each channel, with each spot containing substantially pure protein composition having a unique combination of a particular isoelectric point and a particular molecular weight.

In operation, the buffered, denatured and separated sample reaction product stream is discharged continuously through the nozzle 52 into the receiving apertures 60 as the carriage assembly 48 is advanced along the track 54 from station A to station B. The electrical current flowing through the gel slab 46 causes each protein molecule to migrate through each receiving channel until it reaches the pH gradient point corresponding to its isoelectric value. The molecule becomes immobilized and remains focused at its isoelectric point. Assuming that the molecules which are separated in the column 30 are of the same classification, the molecules will tend to stack vertically in a band cluster C upwardly from the common isoelectric point. As the population of the target molecules increases, the vertical thickness of the band increases. Since the band clusters are presented side-by-side and on a linear time scale, a visual presentation is provided which indicates the effect of a particular agent on a specific kinetic reaction. The molecule population density may be useful for determining the rate of cell formation in the presence of a specific agent, thus indicating the efficacy of the agent for a specific purpose, for example, to promote cell growth or to retard cell growth.

After migration has stabilized, the gel slab 46 may be peeled away from the supporting plates, and the cluster bands in the gel slab are made machine readable or visible by staining with an appropriate die or radioactive marker, so that a protein map is produced. Photographs can be taken to record the protein map, and the protein map may be scanned with an optical densitometer which reduces the protein map to digital data words for computer processing.

While the invention has been shown and described with reference to certain preferred embodiments, it will be understood by those skilled in the art that various changes in forms and details may be made without departing from the spirit and scope of the invention.

What is claimed is:

1. A method for continuous electrophoretic measurement of electrophoretically distinct macro-molecules during a kinetic reaction comprising the following steps:
   (a) continuously drawing a sample stream from a kinetic reaction mixture involving the time variant interaction of macromolecules during a kinetic reaction time interval of interest;
   (b) initiating step (a) not later than the onset of the kinetic time interval of interest and terminating step (a) not earlier than the conclusion of the kinetic reaction time interval of interest;
   (c) continuously depositing the sample stream onto the inlet of an electrophoretic gel slab such that the sample stream is initially deposited on the inlet face on one end of the gel slab and that finally, the sample stream is deposited on the inlet face on the opposite end of the gel slab, with the sample stream being deposited on the slab face between the two end points in a continuous manner; and,
   (d) applying an electric field across the gel slab at a field intensity sufficient to induce movement of macromolecules into the slab.

2. A method for determining the population variation as a function of time of a specific bio-organic component of interest in a mixture which is undergoing a kinetic reaction during a kinetic reaction time interval of interest comprising the steps:
   continuously drawing a sample stream from the kinetic reaction mixture containing the bio-organic component of interest during the course of the kinetic reaction;
   separating a flowing stream of the specific bio-organic component of interest from the kinetic reaction mixture sample stream;
   applying a substantially continuously flowing stream of the separated component of interest along the inlet face of a gel slab, with the separated component stream derived from the kinetic reaction mixture during a first sample interval being deposited on an initial receiving location on the inlet face of the slab, with the separated component stream being deposited continuously on successive receiving locations across the inlet face of the slab, and with the separated component stream being deposited on each receiving location corresponding with successive sample intervals which occur from the onset of the termination of the kinetic reaction time interval of interest; and, applying an electric field across the gel at a field intensity level sufficient to force the separated components from the flowing stream into the slab.

3. A method for determining the population variation as a function of time of a specific bio-organic component of interest in a mixture which is undergoing a kinetic reaction as defined in claim 2, wherein the gel slab has a density gradient which functions as a molecular sieve.

4. A method for determining the population variation as a function of time of a specific bio-organic component of interest in a mixture which is undergoing a kinetic reaction as set forth in claim 2, wherein the gel is buffered to provide isoelectric points distributed substantially uniformly over a predetermined pH range, and including the step of coating the separated components of interest with a denaturing solution so that each separated component of interest exhibits a substantially uniform net surface charge density.

5. A method for determining the population variation as a function of time of a specific bio-organic component of interest in a mixture which is undergoing a kinetic reaction as defined in claim 2, including the steps:

partitioning the face of the gel slab to define a succession of longitudinally spaced receiving apertures along the face of the electrophoresis gel slab; and, controlling the delivery flow rate and the rate of longitudinal travel of the separated component stream relative to the slab so that all of the receiving aperture are filled substantially uniformly and sequentially with the separated component stream being drawn during a corresponding number of successive sample intervals which span an interval from onset to termination of the kinetic reaction time interval of interest.

6. A method for determining the population variation as a function of time of a specific bio-organic component of interest in a mixture which is undergoing a kinetic reaction as defined in claim 2, wherein the separation step is performed by:

producing a continuously flowing eluate stream from a blend of reaction mixture and an eluant; and, forcing the eluate through a high performance liquid chromatography column.

* * * * *